United States Patent [19]

Grabner et al.

[11] 4,415,670

[45] Nov. 15, 1983

[54] MOTIONLESS MIXER AS CELL CULTURE PROPAGATOR

[75] Inventors: Roy Grabner, Blue Bell, Pa.; Edward L. Paul, Chatham Township, Union County, N.J.

[73] Assignee: Merck & Co., Inc., Rahway, N.J.

[21] Appl. No.: 276,418

[22] Filed: Jun. 22, 1981

Related U.S. Application Data

[60] Division of Ser. No. 166,641, Jul. 7, 1980, Pat. No. 4,296,204, which is a continuation-in-part of Ser. No. 872,289, Jan. 25, 1978, abandoned.

[51] Int. Cl.$^3$ ............................................... C12M 3/00
[52] U.S. Cl. ................................... 435/285; 435/284; 435/313
[58] Field of Search ................ 435/287, 285, 284, 313

[56] References Cited

U.S. PATENT DOCUMENTS

| | | | |
|---|---|---|---|
| 3,740,321 | 6/1973 | Pagano et al. | 435/285 |
| 3,785,620 | 1/1974 | Huber | 261/98 X |
| 3,812,016 | 5/1974 | Muller | 435/285 |
| 3,827,943 | 8/1974 | Mann | 435/285 |
| 3,843,454 | 10/1974 | Weiss | 435/285 |
| 3,853,712 | 12/1974 | House | 435/285 |
| 3,871,624 | 3/1975 | Huber | 165/170 X |
| 3,873,423 | 3/1975 | Munder et al. | 435/240 |
| 3,905,865 | 9/1975 | McAleer et al. | 435/285 X |
| 3,918,688 | 11/1975 | Huber et al. | 261/112 |
| 3,933,585 | 1/1976 | McAleer et al. | 435/285 X |
| 3,941,622 | 3/1976 | Munder et al. | 148/27 |
| 3,948,732 | 4/1976 | Haddad et al. | 435/310 X |
| 3,976,547 | 8/1976 | McAleer et al. | 435/285 |

OTHER PUBLICATIONS

Rudiger, "Methods in Cell Biology", Academic Press, (1975), vol. 9, pp. 13–23.
McCoy et al., "Class Helix Perfusion Chamber for Massive Growth of Cells in Vitro", Proc. Soc. Biol. Med., vol. 109, (1962), pp. 235–237.

*Primary Examiner*—R. B. Penland
*Attorney, Agent, or Firm*—Donald J. Perrella; Hesna J. Pfeiffer

[57] ABSTRACT

Use of a static mixing system element as a tissue culture propagator. The element comprises an assembly of parallel sheets shaped to provide a plurality of mixing cells wherein fluid entering a cell from two separate inlet channels is rearranged due to shearing and extensional forces and divided into two new outlet streams each of which leaves the mixing cell in a different direction from either inlet stream. The configuration of the device provides uniform flow across all surfaces for precise control of growth conditions and maximum cell growth.

2 Claims, 1 Drawing Figure

MOTIONLESS MIXER AS CELL CULTURE PROPAGATOR

RELATED APPLICATION

This patent application is a division of Ser. No. 166,461 filed July 7, 1980 now U.S. Pat. No. 4,296,204 which in turn is a continuation-in-part of Ser. No. 872,289, filed Jan. 25, 1978 now abandoned.

BACKGROUND OF THE INVENTION

Human and animal vaccines have been commercially produced by growing the desired virus in primary cells which must be grown on surfaces. Commercial processes were initially developed in Brockway bottles and, as production techniques evolved, the Brockway bottles were replaced by roller bottles. More recently, mass culture systems have been developed, including those which utilize a series of concentric rings or tanks having a plurality of stacked plates. The most recent mass culture system which has been developed is the multiplate machine produced by Biotec A. B. of Sweden which contains a series of titanium discs or plates which are mounted on a rotatable shaft in a cylindrical glass vessel. The vessel is capable of being placed in the upright position, in which the plating surface of the discs is in a horizontal plane in order to permit the cells to settle onto the plating surface of the discs. The device is then placed on its side so that the plated cells are rotated through the growth medium in the vessel until cell sheet formation occurs, the virus seed is then added, the unit is again rotated and the vaccine is harvested. In prior systems of cell cultivation, scale-up to large units has sometimes been difficult as flow patterns at the desired low velocities are not uniform and variations in growth conditions exist.

OBJECTS OF THE INVENTION

It is an object of the present invention to provide an improved apparatus and method for tissue culture propagation. A further object is to provide a tissue culture apparatus and method which provides uniform liquid flow across all growth surfaces. Another object is to provide a tissue culture apparatus and method which provides uniform mixing regardless of flow rate or equipment dimensions. Still another object is to provide a tissue culture apparatus and method which can be scaled-up to large size units without difficulty. These and other objects of the present invention will be apparent from the following description.

DETAILED DESCRIPTION

The present invention relates to a process for producing cells and vaccines, and more particularly, to a process for producing cells and vaccines which utilizes a motionless mixer element as a tissue culture propagator. The motionless mixer element is described and claimed in U.S. Pat. Nos. 3,785,620, 3,871,624 and 3,918,688, the disclosures of which are hereby incorporated by reference. The motionless mixer element is commercially available as the "Koch Static Mixing System", Koch Engineering Co., Inc., New York, a licensee of Sulzer Brothers, Ltd., Winterthur, Switzerland. Briefly, the motionless mixer is an assembly of a plurality of parallel sheets shaped to provide a plurality of mixing cells wherein fluid entering a cell from two separate inlet channels is rearranged due to shearing and extensional forces and divided into two new outlet streams each of which leaves the mixing cell in a different direction from either inlet stream. Each cell is a space formed and bounded by the juncture of two inlet channels and two outlet channels. The two inlet channels converge toward each other at about right angles and the two outlet channels diverge from each other at about right angles. The plane of the inlet channels is rotated about 90° with respect to the plane of the outlet channels and vice-versa. By shearing forces is meant the active mixing resulting from impingement of two streams having different directions of flow. By extensional force is meant the reorientation of outflow at about right angles to the direction of inflow. The static mixing system is used for blending, mixing and dispersing. In addition, Bulletin KSM-2 of Koch Engineering Company Inc. discusses the use of a motionless mixer element as a catalyst support, commenting that the geometrical arrangement of the system "is ideally suited to serve as a catalyst support for any kind of catalytic reaction requiring a narrow residence time distribution and minimized lateral temperature and concentration gradients".

As noted, this invention relates to the use of a motionless mixer element as a support for a tissue culture propagator, the teaching in prior art of the use of the system as a catalyst support is the closest use to that of applicants. However, even though this use is as a support, it is much different in the sense that the primary cells are growing organisms attached to the surface. These cells must be provided with uniform medium flow at a low velocity across all the surfaces in order to precisely control growth conditions and maximize cell growth. Human and animal vaccines have been commercially produced by growing the desired virus in primary cells which must be grown on surfaces.

We have now found that high production can be achieved by using the surfaces of a motionless mixer element as a cell growth surface. Mammalian cells are attached to the mixing elements by slow rotation of the elements. During the subsequent cell replication phase, nutritional requirements of the cells are supplied by circulating fluid through the mixing elements. The system, even though operated in a laminar flow region, is capable of supporting high density cell growth. In addition, the conditions in the motionless mixer element can be effectively scaled-up for large scale production operations.

The advantage of the use of a motionless mixer element in the production of live cells for vaccine use is that the unique mixer element design acts as a simple stationery baffle that utilizes the energy of the flowing fluids to produce mixing resulting in consistent performance regardless of flow rate and equipment dimensions. These well-defined flow characteristics and compactness permit operation in circulating modes with wide range of flow rates and excellent control of growth conditions. These characteristics are also beneficial when washing cells of undesirable materials.

The process of the present invention may be used to produce viral vaccines such as measles, mumps, rubella, Marek's disease, Herpes simplex types I and II, influenza, parainfluenza, varicella, cytomegalo, hepatitis A, hepatitis B and respiratory syncytial and cells such as chick embryo and duck embryo cells and cell lines such as WI38, VIRO, Hela, Standard cells, sera, and media may be used to charge the propagator. For example, primary cells such as chick embryo fibroblasts, green monkey kidney, bovine kidney, dog kidney cells or diploid cells such as WI-38 may be utilized as may standard sera such as fetal calf, calf, bovine, G-G-free new born calf, α-gamma calf or α-gamma bovine and standard media such as Eagles Basal Medium, Medium 199, Medium EBME, Eagle's Miminum Essential Medium (EMEM), and Medium O.

In one embodiment, as described in U.S. Pat. No. 3,871,624, a motionless mixer element is formed of layers of flat thin plates to which flat thin guide elements disposed at an angle are connected, so that the flat thin plates bound the various flow channels on one side, and two parallel adjacent guide or deflector elements in each case bound the flow channels on two other sides. For instance, the guiding or deflecting elements on a layer can have a herringbone pattern.

In another embodiment, each layer of the mixing element comprises a tube bank in which the tubes form the flow channels and contact one another longitudinally, the tubes of at least any two adjacent tube banks may communicate with one another by way of aperatures.

In one advantageous embodiment of the mixing device, as described in U.S. Pat. No. 3,918,688, the layers of the insert consist of corrugated sheets which contact one another with the corrugations of adjacent sheets situated at an angle to the longitudinal axis of the mixing device, as considered in the direction of flow of the flowing media.

In another advantageous embodiment, the individual layers of an insert may be formed from plane surface elements to which sheet-like guide elements inclined at an angle are connected so that the individual flow ducts are bounded by the plane surface elements and by each pair of parallel adjacent guide elements. By way of example, the guide elements may extend in the form of a fishbone on a layer.

The process of the present invention will be better understood by an examination of the accompanying drawing in which:

FIG. 1 is a schematic view of the cell propagation system using a motionless mixer element. The growth medium reservoir 10 is fitted with a medium conduit 11, inlet 27, return 19, and vent 28. The inlet 27 provides an air inlet 23 and an air/CO$_2$ inlet 25, connected through two flow meters 24 and 25 respectively, so that gas intake into the medium reservoir is controllable. The medium conduit 11 can be divided into a multiple of feed streams. Two are illustrated, going through pumps 12 and 13 to two motionless mixer elements 14 and 15. A sampling outlet is provided at 16. Following residence in the motionless mixer elements, and return 19 which is fitted with a sampling point 20, dissolved oxygen monitor 21, and inlet 22 (for fresh media or viruses) the medium is returned to the medium reservoir 10 via return 19, providing the recyclable closed system.

The operation of the system involves pumping a previously prepared cell suspension into the motionless mixer element, then pausing to let the cells settle on the surface. Following a residence time of 5-30 hours, during which the units are shifted and rotated occasionally, cell growth is initiated. The end of the attachment is determined by monitoring cell counts of the fluid recovery sample outlet 16. Cell growth is initiated and supported by circulating the desired medium through the system. Monitoring control of the growth phase is achieved by controlling of dissolved oxygen levels at 1 to 10 ppm and pH at 5 to 8 throughout. The end point is reached by monitoring the glucose concentration, which drops from 1 to 0.01 mg/ml. The cells are then stripped from the motionless mixer element by charging with trypsin and recovering following usual procedures.

This invention also relates to production of vaccines by growing the cells in the motionless mixer, then seeding with the desired virus, propagating and harvesting.

The following examples illustrate the present invention without, however, limiting the same thereto.

EXAMPLE 1

Eleven day chicken embryos are aseptically removed, decapitated, washed, minced and then trypsinized, for 2 hours at 37° C. The slurry is strained to remove debris after which the slurry is centrifuged to collect the cells. The supernatant liquid is decanted and the cells (pellet) resuspended in Medium "O" with 10% fetal calf serum. A total of 12 embryos are processed yielding $1,200 \times 10^6$ cells. These are further diluted with Medium "O" containing 2% fetal calf serum for a final concentration of $1.8 \times 10^6$ cells/ml ready for addition to the motionless mixer.

The motionless mixer is assembled by inserting 5 and 6 2-inch titanium elements (Type CY=900 cm$^2$/element) in each of two 12" sections of 2" glass pipe with end plates. These units have been cleaned with acid and base and flushed with copious quantities of distilled water. Tubing is attached to the end of the fetal calf serum and incubated at 37° C. for 3 days. Medium is drained from units and retained as sterility test. Cell suspension is now introduced into the mixing units with 275 ml and 300 ml charged to units containing 5 and 6 elements respectively. The partially filled units contain ca. 200 ml of air. Uniform cell attachment is carried out by adjusting the motionless mixer to horizontal position and rotating at 6 minutes per revolution for 6 and 17 hours for 6 and 5 element units respectively. Subsequently, the motionless mixer is adjusted to vertical position and medium with unattached cells drained. Cell counts of this fluid recover 15% and 33% of input cells from 5 and 6 element units respectively. Cell growth is now initiated by connecting units to a medium reservoir containing 2.6 l of Medium "O" with 2% fetal calf serum and medium is circulated through units at initial rate of 40 ml/min. Medium reservoir is aerated with air/CO$_2$ mixture to maintain pH and dissolved oxygen. Growth phase is continued for 72 hours during which time medium circulation is gradually increased to 70 ml/min for a nominal residence time of 7 minutes. Excellent control is attained as dissolved oxygen remains at 5 to 6 ppm and pH is controllable at pH 7.0 to 7.3 by varying aeration rates. Glucose concentration in medium drops from 0.9 to 0.4 mg/ml during growth phase. Cells are stripped from the surface by charging 300 ml of trypsin at 37° C. to the motionless mixer and rotating at 1/6 RPM for 15 minutes. Trypsin was neutralized with fetal calf serum and detachment completed by rotating units end over end ca. 6 times for additional mixing. Cell count for this solution shows recovery of $1.1 \times 10^9$ cells and cell densities of 200,000 cells/cm$^2$.

EXAMPLE 2

A cell suspension is prepared by the process of Example 1. A total of 30 embryos are processed yielding $3.45 \times 10^9$ cells which are diluted to a final concentration of $4.8 \times 10^6$ cells/ml for planting.

The motionless mixer is again assembled with 6 2-inch Type CY titanium elements in two sections of pipe, one glass and one stainless steel. Tubing is attached to the clean units. After autoclaving, the mixer is preincubated at 37° C. for 3 days. The mixers then are each charged with 300 ml of cell suspension (equivalent to 13 embryos) and rotated at 1/6 RPM for 7 hours at 37° C. to complete attachment. The mixers are subsequently drained to remove unattached cells (ca. 16% of input). Growth phase is then continued by adjusting the motionless mixers in vertical position and connecting to medium reservoir containing 3.0 l of Medium "O" with 2% fetal calf serum. Medium is circulated through the mixers in parallel at initial rate of 50 ml/min which is gradually increased to 80 ml/min. Medium reservoir is aerated with air/$CO_2$ mixture to control pH 7.0 to 7.4 and dissolved $O_2$ at ca. 5 ppm during growth cycles. Rapid consumption of glucose at these high loadings necessitates complete replacement of medium after 50 hours and 68 hours of growth. Units are harvested with trypsin after 89 hours. Cell yields are 2.3 and $2.5 \times 10^9$ cells for cell densities of 450,000 cells/$cm^2$.

EXAMPLE 3

A cell suspension is prepared from 11 day chicken embryos by the procedure of Example 1. A total of 30 embryos are processed yielding $3.0 \times 10^9$ cells which are diluted to a final concentration of $4.3 \times 10^6$ cells/ml for planting.

The motionless mixer is assembled by inserting 6 2-inch Type CY titanium elements in each of two 12.5" sections of 316 stainless steel pipe. As usual, alternate elements are rotated 90° to achieve optimal mixing. Units are cleaned in place, autoclaved and preincubated at 37° C. Units are charged with 300 ml of cell suspension (equivalent to 13 embryos) and rotated 1.6 RPM for 7 hours at 37° C. in horizontal position. The mixers are then returned to vertical position, drained and connected to medium reservoir containing 3.0 l of Medium "O" with 2% fetal calf serum. Medium is circulated through each unit at a rate of 30 ml/min which is gradually increased to 80 ml/min corresponding to 15 minutes and 6 minutes nominal residence time respectively. The medium reservoir is aerated with air/$CO_2$ to control pH in the range of 6.9 to 7.5 during growth phase that is continued for 96 hours (4 days). The mixers then are drained and fresh medium added after 53 hours and 78 hours to maintain adequate nutrient supply for cells. After 91 hours, one mixer is harvested with trypsin yielding $1.8 \times 10^9$ cells for cell density of 350,000 cells/$cm^3$. After 96 hours the second unit is drained and seeded with Herpes Simplex Type I virus. Seed is prepared by disrupting a sample of infected cells by sonication and diluting in Medium "O" so that $1.5 \times 10^8$ plaque forming units (PFU) of virus are available in 500 ml of medium. The mixers are charged in vertical position and incubated at 37° C. for one hour for virus attachment to cell layer. Medium is then diluted to 1,000 ml in medium reservoir and circulated through unit at 50 ml/min for another hour. Medium volume is increased to 3,800 ml and circulation maintained at 60 ml/min for 48 hours. Infected cells are harvested at this time by draining one-half of medium from the mixers and then turning the mixers end over end so that the two phase solution (medium/air) rapidly rushes through the mixer elements. Medium is now drained for assay. The solution contains $2 \times 10^{11}$ PFU for a substantial virus production.

What is claimed is:

1. A motionless mixer element for propagating tissue culture cells, said mixer element being disposed within a housing and comprising an assembly of parallel sheets shaped to provide a plurality of channels which converge and diverge to form a plurality of mixing cells, each cell being formed and bounded by the juncture of two inlet channels which converge toward each other at about right angles in one plane, and two outlet channels which diverge from each other at about right angles in another plane, the planes being rotated about 90° with respect to each other, the cells being adapted to receive a fluid entering a cell in two separate inlet streams and to rearrange the fluid due to shearing and extensional forces and to direct the fluid exiting the cell into two outlet streams each of which leaves the cell in a direction different from either inlet stream, and tissue culture cells attached to the assembly of parallel sheets.

2. A motionless mixer element according to claim 1 wherein the tissue culture cells are infected with a virus.

* * * * *